United States Patent [19]

Robinson et al.

[11] Patent Number: 4,559,044
[45] Date of Patent: Dec. 17, 1985

[54] VOLUMETRIC METERING UNIT FOR INTRAVENOUS FLUID ADDITION

[75] Inventors: Thomas P. Robinson, Plano; Don M. Killman, Balch Springs; Andrew P. Mattson; James E. Hudson, Jr., both of Dallas, all of Tex.

[73] Assignee: Quest Medical, Inc., Carrollton, Tex.

[21] Appl. No.: 404,811

[22] Filed: Aug. 3, 1982

[51] Int. Cl.[4] .............................................. A61M 5/00
[52] U.S. Cl. ..................................... 604/246; 604/65; 222/450
[58] Field of Search ................................ 604/65–67, 604/151–153, 246, 250; 222/450

[56] References Cited

U.S. PATENT DOCUMENTS

| | | | |
|---|---|---|---|
| 3,575,161 | 4/1971 | London | 604/250 X |
| 4,121,584 | 10/1978 | Turner et al. | 604/246 |
| 4,181,245 | 1/1980 | Garrett et al. | 222/450 |
| 4,204,538 | 5/1980 | Cannon | 604/246 |
| 4,391,598 | 7/1983 | Thompson | 604/65 |

Primary Examiner—Dalton L. Truluck
Attorney, Agent, or Firm—Richards, Harris, Medlock & Andrews

[57] ABSTRACT

Three embodiments of a metering unit (10, 140, 200) are provided for metering fluid from a container (14) for infusion into a patient. The first embodiment of the metering unit (10) includes a cassette (26) formed of halves (28, 30). The halves (28, 30) each have a concave reservoir portion (36) formed on the inner face (32) thereon. Entry and exit channels (38, 42) extend from the reservoir portions adjacent entry and exit orifices (40, 44). Entry and exit port portions (46, 50) are formed in each half (28, 30). Flexible entry and exit valves (58, 64, 86 and 88) are movable between an open position, permitting fluid to flow through the orifices, to a closed position, preventing fluid from flowing through the orifices. The halves are separated by a flexible diaphragm (70) which divides a reservoir (76) into first and second compartments (78, 80). One entry valve is opened to permit fluid from the entry port (82) to flow into one compartment, the fluid flowing into the compartment moving the flexible diaphragm to force the fluid in the other compartment out to the exit port (84). The position of the valves is then interchanged, permitting fluid to flow into the other compartment and forcing the fluid in the first compartment into the exit port. A cassette (206) in the third embodiment of the unit (200) includes identical halves (208, 210) sonically bonded together. A diaphragm (296) separates parallel channels (218, 222) to reduce head pressure channel volume variations. Grooves (228, 230) are provided in the reservoir portions (216) to prevent fluid trappage between the diaphragm and portion wall. In all cassette embodiments, an activating frame operating the cassette prevents the positioning of all valves in the open position simultaneously.

38 Claims, 21 Drawing Figures

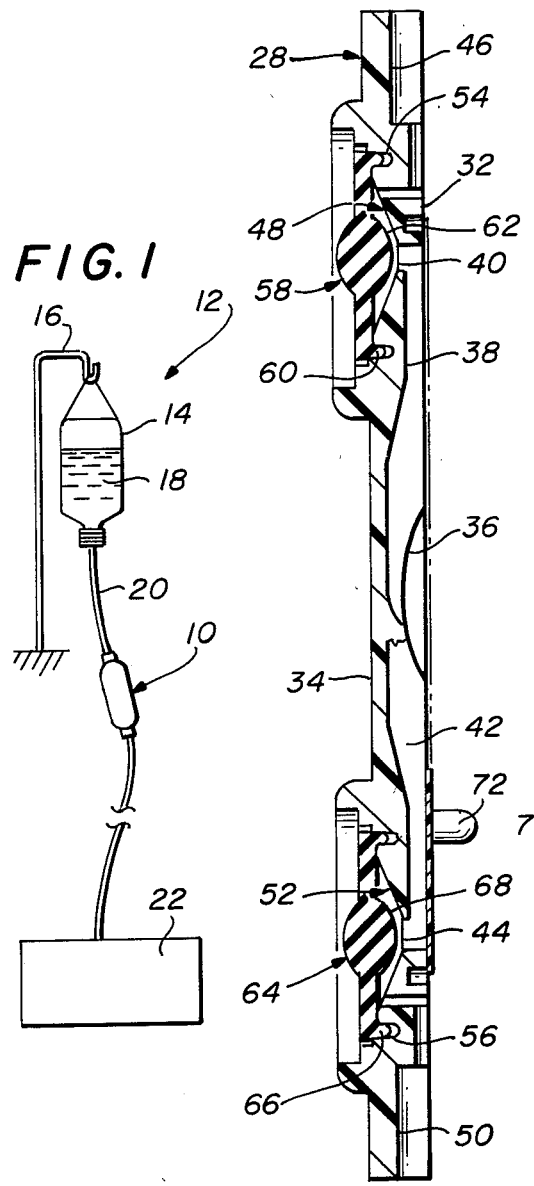

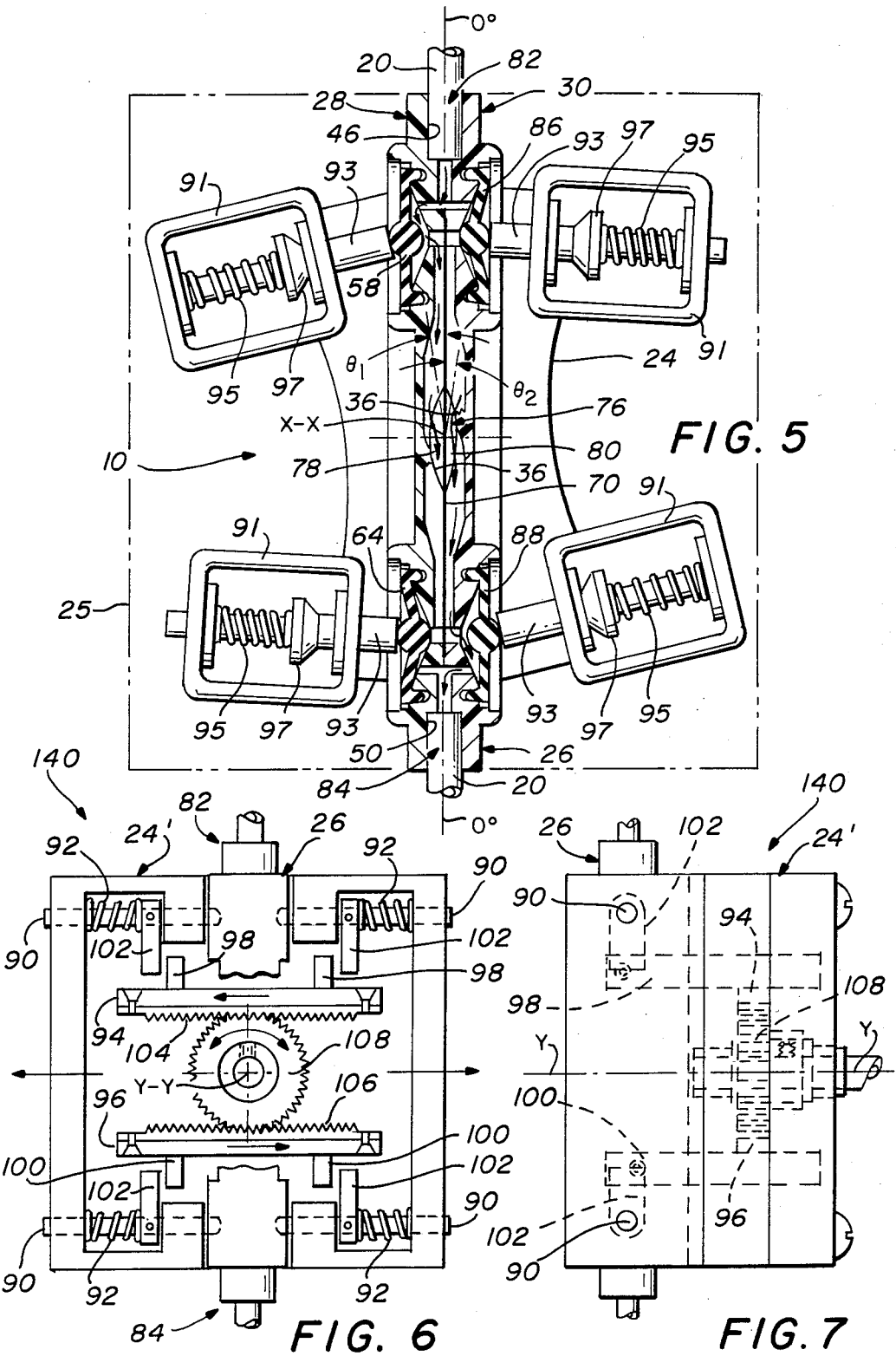

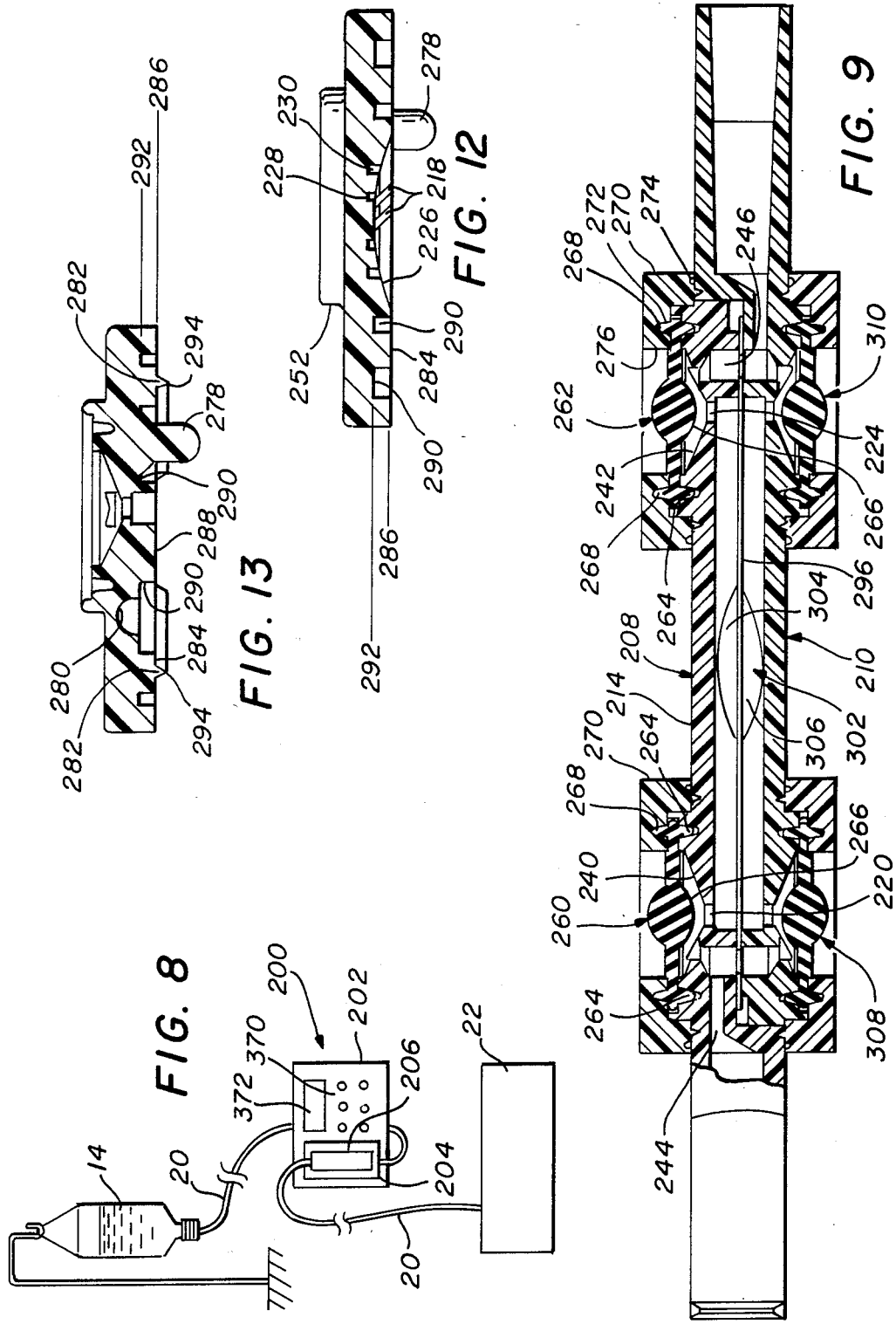

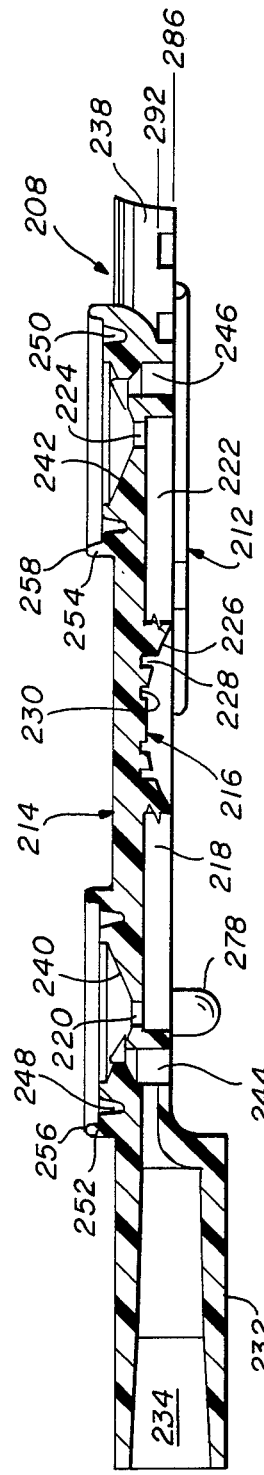
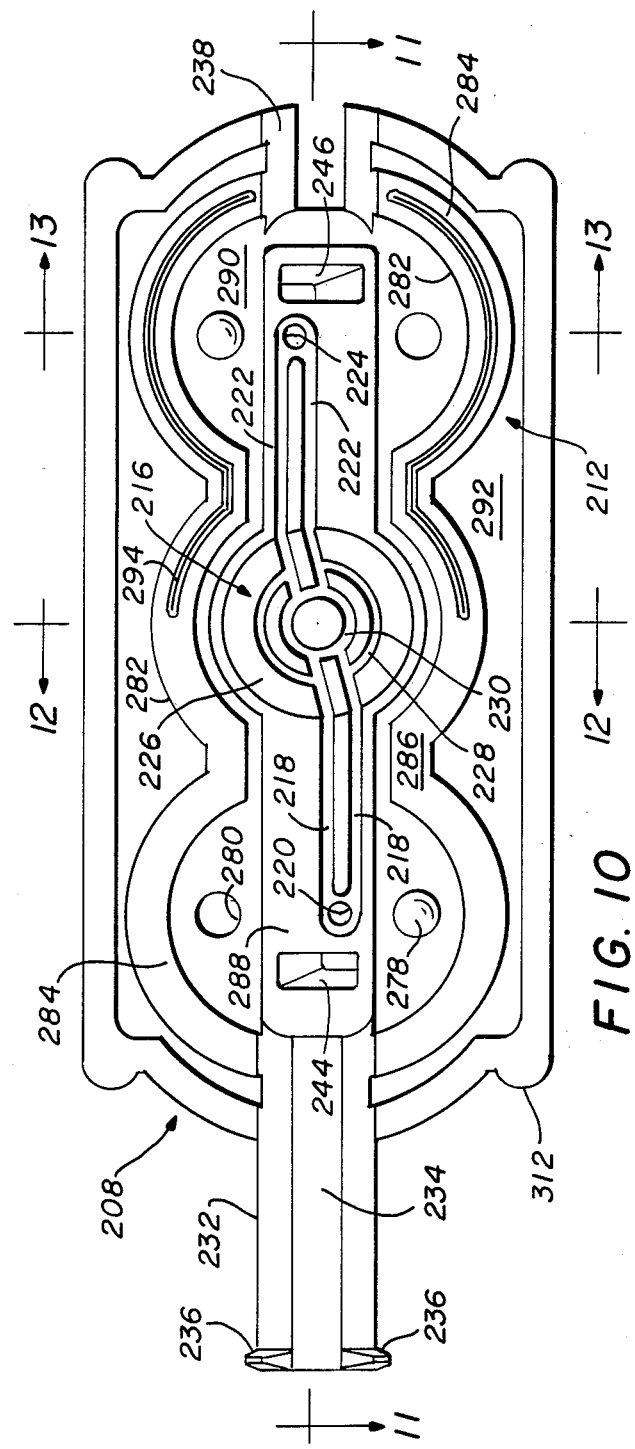

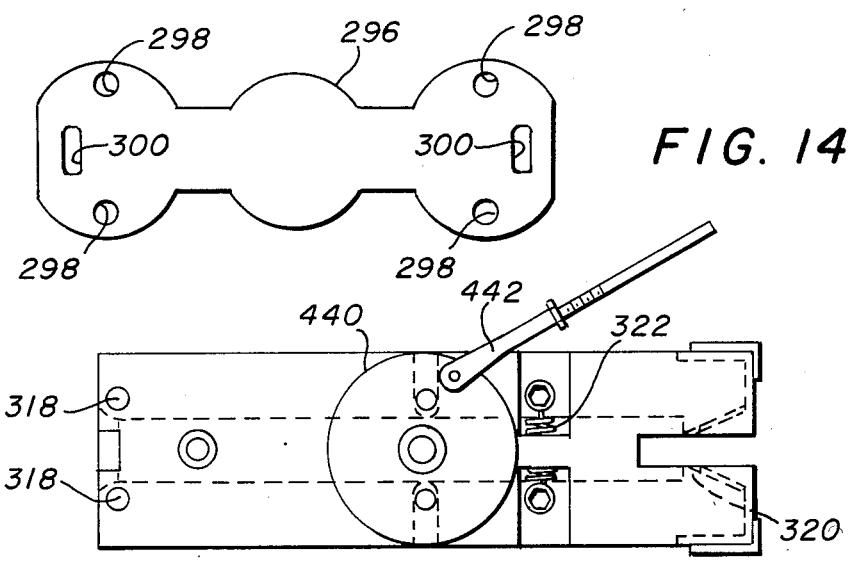
FIG. 14
FIG. 16
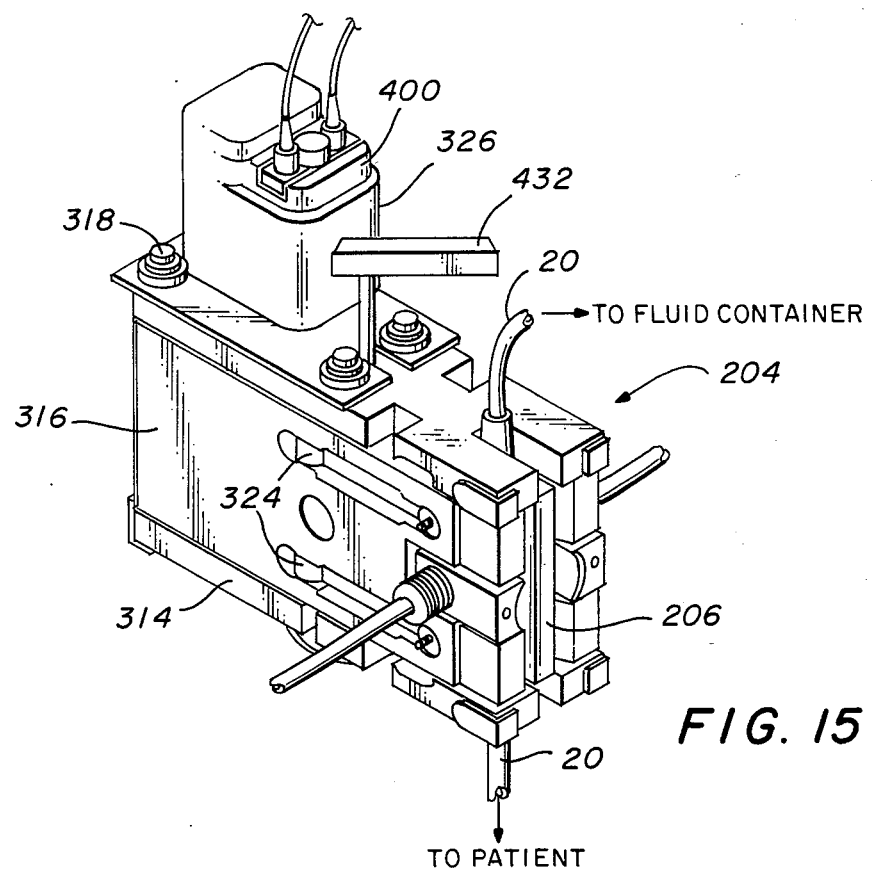
FIG. 15

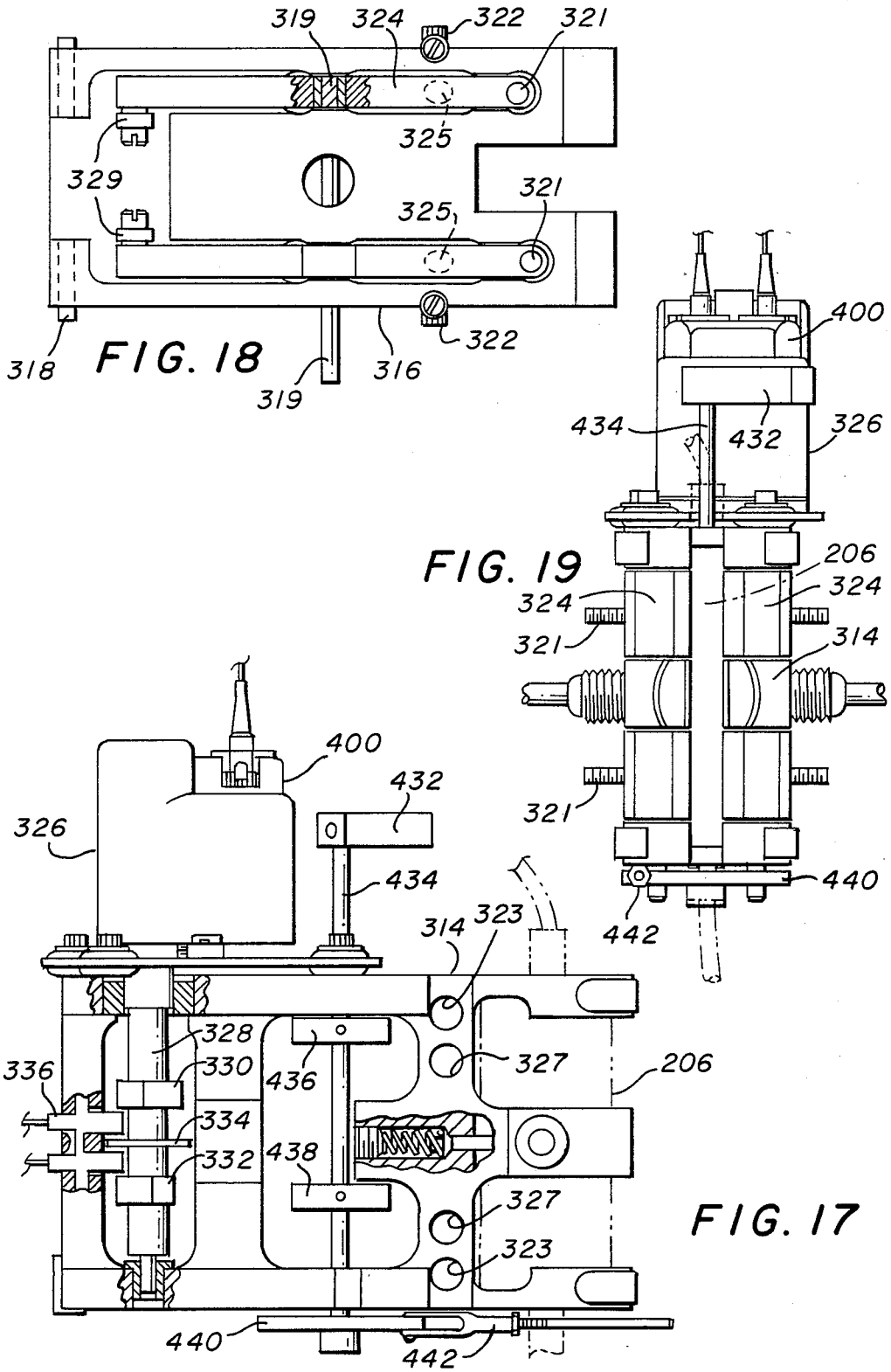

VOLUMETRIC METERING UNIT FOR INTRAVENOUS FLUID ADDITION

TECHNICAL FIELD

This invention relates to the metering of fluids, and in particular, to the metering of intravenous fluids to a patient.

BACKGROUND ART

Intravenous fluid or drug additive systems have been used in patient care for many years. The systems typically operate by gravity induced flow from a container positioned above the patient.

Traditionally, the flow rate of the fluid from the container was measured with a drip chamber at the container and controlled by a clamp varying the restriction in a delivery line extending between the drip chamber and the patient. A nurse or aide visually counts the drop rate in the drip chamber and manually sets the clamping or pinching device to achieve a desired flow rate. The accuracy of this system assumes the consistency in volume of each drop of fluid into the drip chamber. However, the drop size is dependent on the orifice diameter in the drip chamber which varies within a manufacturing tolerance for a particular container. Even the nominal orifice diameter is not uniform throughout the industry. Manufactures sell drip chambers having 10, 15, 20 and 60 drop per milliliter chambers, for example. In addition the volume of the drops may vary with temperature, viscosity and rate.

The pinching device may also induce error in the flow rate. For example, the tubing adjacent the pinching device may relax, altering the restriction to flow and permitting variation in the flow rate from the desired value. The gravitational head pressure acting to infuse the fluid into the patient may also vary. For example, the patient may turn over, sit up or roll on the delivery line to further restrict flow.

One attempt to overcome several deficiencies in delivery systems including a drip chamber is disclosed in U.S. Pat. No. 4,204,538, issued May 27, 1980 to Raymond E. Cannon. This patent discloses a cassette which provides for controlled introduction of fluid from a container to the patient. A chamber is provided which is divided into two compartments by a flexible separating member. The separating member is attached at its periphery to the walls of the chamber and is movable between the end walls defining the boundaries of the compartments. Conduits lead to each of the compartments from a container with a valve positioned in each conduit. Branch lines extend from each of the compartments to the patient with a valve being positioned in each line. The valve operation is sequenced so that fluid flow comes into one chamber from the container while fluid leaves the other chamber for delivery to the patient. The separating member flexes to enlarge the volume of the filling compartment and decrease the volume of the compartment flowing to the patient. However, the rate of flow of the fluid is controlled by setting a pinch clamp.

The construction of the cassette includes four individual segments in facing relationship. Each of the segments has a complex shape. This results in high manufacturing costs. Each of the valves positioned in the cassette are positioned for activation by parallel reciprocating rods. The cassette must remain stationary while each rod activates its associated valve.

A need has arisen for a metering unit which overcomes the problems associated with the drip chamber and variation in drip volume. Finally, a metering unit is needed which accurately performs the function of metering fluid to the patient in a cost effective manner.

SUMMARY OF THE INVENTION

In accordance with the present invention, an apparatus for metering a fluid therethrough is provided. The apparatus includes first and second halves adapted to be secured in facing relation. Each of the halves is constructed to form a reservoir portion, inlet and outlet channels extending from the reservoir portion and inlet and outlet port sections. The inlet and outlet channels and inlet and outlet port sections are interconnected by inlet and outlet orifices, respectively. The reservoir portions form a reservoir and the inlet and outlet port sections form entry and exit ports when the halves are secured in facing relation. A flexible diaphragm structure is positionable between the halves to divide the reservoir into first and second compartments.

A first entry valve and first exit valve are attached to the first half. Each of the first entry and exit valves is movable from an open position permitting flow through the inlet and outlet orifices, respectively, to a closed position to prevent flow therethrough. A second entry valve and second exit valve are attached to the second half. The second entry and exit valve means are each movable from an opened position permitting fluid flow through the inlet and outlet orifices in the second half, respectively, to a closed position preventing flow therethrough.

Activating structure may be used for alternately opening and closing each of the valves. The first entry valve and second exit valve are opened and closed simultaneously. The second entry valve and first exit valve are also opened and closed simultaneously and opposite the first entry valve and second exit valve. Fluid entering the entry port flows through the inlet orifice and inlet channel of the first half to the first compartment when the first entry valve is opened. The fluid entering the entry port has a higher pressure than the fluid in the second compartment to move the diaphragm structure to force the fluid in the second compartment through the outlet channel and outlet orifice of the second half.

Fluid entering the entry port flows through the inlet orifice and inlet channel of the second half into the second compartment when the second entry valve is open. The fluid entering the entry port has a sufficient higher pressure than the fluid in the first compartment to move the diaphragm structure to force the fluid in the first compartment through the outlet channel and outlet orifice of the first half. The volume of the fluid displaced from each of the first and second compartments is predetermined.

In accordance with another aspect of the present invention, the first and second halves of the apparatus for metering a fluid therethrough are identical.

In accordance with another aspect of the present invention, each of the halves include a plurality of inlet and outlet channels. This acts to reduce potential variation in the cross-sectional area of the channels by head pressure variable deflection of the diaphragm into the channels. The inlet and outlet channels in each half can also be offset so that when the halves are in facing relationship, there are no channels on directly opposite side of the diaphragm. This again serves to reduce potential variation in the cross-sectional areas of the channels.

The apparatus performs the metering function using only two halves. This is an improvement over the prior known apparatus where four pieces having more complex shapes are required.

In accordance with yet another aspect of the present invention, frame structure is mounted for movement relative to the first and second halves when in the facing relation. A plurality of rod structures are positioned on the frame structure. A rod structure contacts each of the valve structures for operating the valve structure between open and closed positions. The movement of the frame structure relative to the first and second halves permits the fluid to flow from the first and second compartments to the exit port.

In accordance with yet another aspect of the present invention, the rod structure positioned on the frame structure maintains each of the valve structures in the closed position when inactivated to block fluid flow to the patient.

In accordance with yet another feature of the present invention, the apparatus includes frame structure fixed relative to the halves in the facing relation. A plurality of rod structures are mounted to the frame structure, a rod structure contacting each of the valve structures. A drive structure is provided to move the rod structures to activate the apparatus to permit fluid to flow into the first and second compartments and meter fluid from the first and second compartments to the exit port. The rod structures can also maintain the valves in the closed position to prevent fluid flow therethrough when the apparatus is not activated.

In still another embodiment of the present invention, an apparatus is provided for activating a cassette. The cassette has inlet and outlet ports and at least two flow paths therebetween. Each of the flow paths within the cassette has entry and exit valve structure actuatable between open and closed positions for blocking fluid flow along the flow paths in the closed position. The apparatus includes a frame and clamp structure for securing the cassette in a fixed relation to the frame. Actuator structure is provided for actuating the valve structures. The actuating structure prevents the simultaneous positioning of the entry and exit valve structure in a given flow path in the open position to prevent uncontrolled fluid flow through the cassette.

BRIEF DESCRIPTION OF THE DRAWINGS

A more complete understanding of the invention and its advantages will be apparent from the following Detailed Description when taken in conjunction with the accompanying Drawings, in which:

FIG. 1 illustrates a fluid delivery system incorporating a metering unit forming one embodiment of the present invention;

FIG. 2 illustrates an inside view of one half of a cassette used in the metering unit;

FIG. 3 illustrates a vertical cross-sectional view of the half taken along line 3—3 in FIG. 2 in the direction of the arrows;

FIG. 4 is an end view of the half taken along line 4—4 in FIG. 2 in the direction of the arrows;

FIG. 5 is a front view of a metering unit forming the first embodiment of the present invention;

FIG. 6 is a front view of a metering unit forming a second embodiment of the present invention;

FIG. 7 is a side view of the metering unit forming the second embodiment of the present invention;

FIG. 8 illustrates a fluid delivery system incorporating a metering unit forming a third embodiment of the present invention;

FIG. 9 illustrates a vertical cross-sectional view of the cassette used in the third embodiment;

FIG. 10 is an inside view of the one half of the cassette used in the third embodiment;

FIG. 11 is a vertical cross section of one half of the cassette taken along line 11—11 in FIG. 10 in the direction of the arrows; FIG. 12 is a vertical cross section view of one half of the cassette taken along line 12—12 in the direction of the arrows in FIG. 10;

FIG. 13 is a vertical cross section view of one half of the cassette taken along line 13—13 in the direction of the arrows in FIG. 10;

FIG. 14 is a top view of the diaphragm employed with the cassette in the third embodiment;

FIG. 15 is a perspective view of an actuating mechanism for the cassette in the third embodiment;

FIG. 16 is a bottom view of the actuating mechanism for the cassette of the third embodiment;

FIG. 17 is a side view of the frame in the actuating mechanism in partial cross section;

FIG. 18 is a side view of one clamshell portion of the actuating mechanism;

FIG. 19 is an end view of the actuating mechanism;

DETAILED DESCRIPTION

Figure 20:
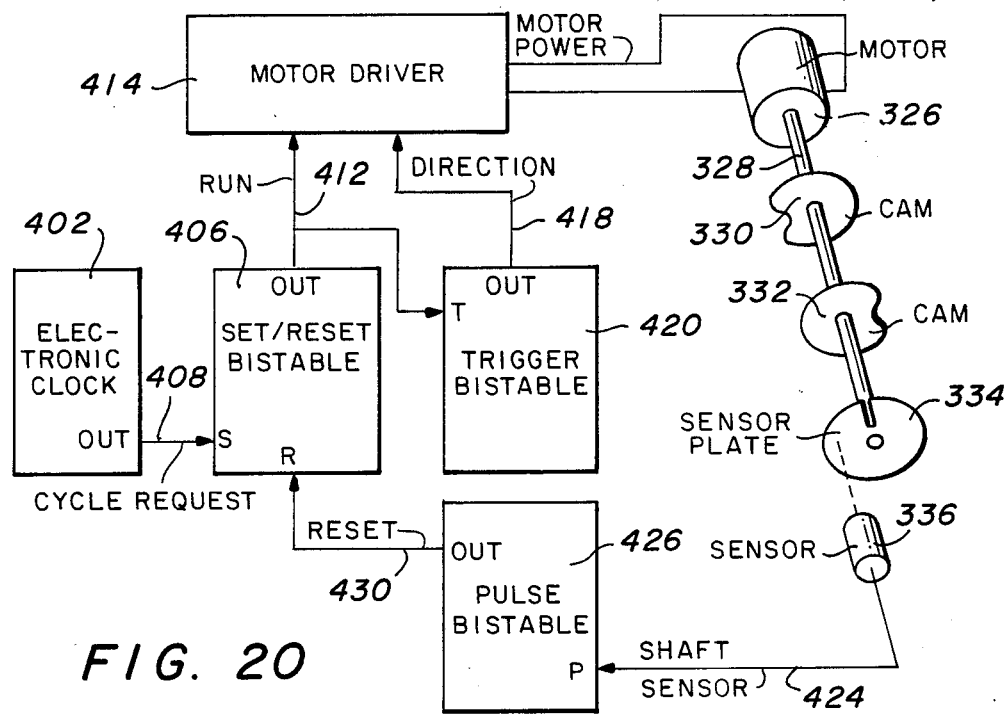
FIG. 20 is a block diagram of an electronic control circuit employed with the actuating mechanism.

Referring now to the Drawings, wherein like reference characters designate like or corresponding parts throughout several views, a first embodiment of the present invention is formed by metering unit 10 which is illustrated in FIGS. 1-5 and described hereinafter. The metering unit 10 provides for a volumetrically controlled introduction of fluid from a container to a patient in the intravenous additive system 12 shown in FIG. 1. A container 14 is suspended from a rod 16 as shown. The fluid 18 to be infused is stored within the container 14. A delivery line 20 extends from the container 14 to the patient 22. The metering unit 10 is positioned within the delivery line 20. It will be observed that the fluid 18 and container 14 are positioned above the metering unit 10 and patient 22 to provide a fluid pressure head to permit the metering unit 10 to function properly and infuse fluid into the patient. However, the metering unit 10 can be positioned above fluid 18 and container 14 provided that the patient is still below container 14 with continuous fluid flow between the container and unit 10.

The metering unit 10 includes a frame 24 mounted in structure 25 and a cassette 26 positioned therein as best shown in FIG. 5. Also provided are electronics or other apparatus to operate the unit in the manner described hereafter.

The cassette 26 comprises two halves 28 and 30. The cassette 26 has the significant advantage over prior known designs in performing the function noted hereafter while comprising only two halves 28 and 30. As will be apparent from the discussion hereafter, the halves 28 and 30 are readily adapted for inexpensive, quantity production. Half 28 is illustrated in FIGS. 2-4 and will be described hereinafter. In the preferred construction, the halves 28 and 30 are identical to reduce manufacturing costs. It will be understood that the description of half 28 will be equally applicable to half 30.

The half 28 includes an inner face 32 forming one side thereof. An outer face 34 is formed on the opposite side. A concave reservoir portion 36 is formed within the inner face 32 as shown in FIGS. 2 and 3. An entry channel 38 is also formed in the inner face 32 which extends from the reservoir portion 36 to an entry orifice 40 as shown in FIGS. 2 and 3. An exit channel 42 is similarly formed within the inner face 32 which extends from the reservoir portion 36 to an exit orifice 44. Both channels 38 and 42 are offset from the elongate centerline of the half 28. In the preferred construction, the cross-sectional area of the entry and exit channels opening through the inner face 32 is minimized.

An entry port portion 46 is formed in inner face 32 at the end of the half 28 near entry orifice 40. The entry port portion 46 has one end opening through a seal surface 48 surrounding the entry orifice 40 and formed in the outer face 34.

A similar exit port portion 50 is formed in the inner face 32 of the half 28 near the exit orifice 44. One end of the exit port portion extends through a seal surface 52 surrounding the orifice 44 and formed in the outer face 34.

Annular notches 54 and 56 are formed in the outer face 34 and are concentric with the entry and exit orifices 40 and 44, respectively. In the preferred construction, the halves 28 and 30 are molded of a suitable plastic. The configuration of the inner and outer surfaces of the halves do not require the use of movable insert pins in the molding operation. This represents a significant cost advantage.

An entry valve 58 formed of an elastomeric material is provided with a lip 60 for sealing engagement within the annular groove 54. The entry valve 58 includes a hemispherical sealing face 62 which may be moved into sealing engagement with the seal surface 48. An exit valve 64 is provided with lips 66 for sealing engagement in the annular groove 56. The exit valve 64 includes a hemispherical sealing face 68 for sealing engagement with the seal surface 52.

The inner faces of the two halves 28 and 30 are designed to be secured in a facing relation and separated by a flexible diaphragm 70. Suitable pins 72 and apertures 74 are provided on both halves 28 and 30 to properly align the halves in the facing relation. The halves may be maintained in this relation by any common means, such as glue, ultrasonic bonding, threaded screws, rivets, bolts, or even injection molded together, etc.

When the halves 28 and 30 are in the facing relation to form cassette 26 as best shown in FIG. 5, the concave reservoir portions combine to form a concave reservoir 76 separated into a first compartment 78 and a second compartment 80 by the flexible diaphragm 70. The flexible diaphragm 70 also prevents fluid flow between the channels 38 and 42 within either half. The entry port portions 46 of each half combined to form an entry port 82. The exit port portions 50 of the two halves combine to form an exit port 84.

When the entry valve 58 and exit valve 64 on half 28 and entry valve 86 and exit valve 88 on half 30 are in the open position, as shown in FIG. 3, fluid flow is permitted through the associated ports and orifices. The released position of the valves is also the open position. When the valves are deflected inward by an external influence toward the inner face of the half to which they are secured, the valve will close and prevent fluid flow through the associated ports and orifices. Exit valve 64 and entry valve 86 are shown in the closed position in FIG. 5.

In the first embodiment, frame 24 is movable relative to the cassette 26 about an axis X—X centered through the reservoir 76 in the cassette. The range of motion extends to angles $\theta_1$ and $\theta_2$ on either side of zero deflection. Frame 24 is shown in FIG. 5 pivoted to angle $\theta_1$. Members 91 are positioned at the four corners of the frame 24 for guiding and supporting rods 93. The rods 93 are urged toward the cassette by springs 95 acting between the members 91 and collars 97 on each of the rods. The tip of each of the rods lies adjacent a valve in cassette 26.

When frame 24 is centered with respect to the cassette 26 at zero deflection, the springs 95 urge the rods 93 into engagement with the associated valves to close the valves and prevent fluid flow through the cassette. The metering unit may be activated if the frame 24 is pivoted clockwise or the cassette 26 counterclockwise to the $\theta_2$ position. It will be seen that the rods acting on exit valve 64 and entry valve 86 will be withdrawn to permit the valves to move to the open position. The entry valve 58 and exit valve 88 are retained in the closed position. The metering unit may again be activated by moving frame 24 to the $\theta_1$ position as shown in FIG. 5, opening valves 58 and 88 and closing valves 64 and 86. Activation of the metering unit to open and close the alternate pairs of valves will permit the metering of the predetermined volume of fluid into the exit port 84 for infusion into the patient upon each activation thereof. The rods 93 and springs 95 can be designed to prevent the valves 58, 64, 86 and 88 from being open simultaneously in any position, even when the frame 24 is centered between the $\theta_1$ and $\theta_2$ positions.

A first modification of the present invention is illustrated in FIGS. 6 and 7 and comprises a metering unit 140. The metering unit includes the cassette 26 described with reference to the first embodiment above.

When cassette 26 is positioned within frame 24', a plurality of rods 90 are urged by springs 92 to engage each of the valves to move the valves into the closed position. Upper and lower gear racks 94 and 96 are slidably supported by the frame 24' for motion perpendicular to the elongate direction of the cassette. Each of the gear racks includes extensions 98 and 100 for cooperation with the extensions 102 on the rods 90. The gear racks 94 and 96 include gear teeth 104 and 106 for engaging the teeth of a gear 108 mounted for rotation about an axis Y-Y relative to the cassette.

It will be clear from FIGS. 6 and 7 that rotation of the gear 108 in a first direction, such as the clockwise direction as viewed in FIG. 6, upon activation of metering unit 140, will urge the upper gear rack 94 to the right and the lower gear rack 96 to the left. The extensions 98 and 100 thereof will engage extensions 102 of the rods 90 at opposite corners of the frame which permit the associated valves 64 and 86 to move to the open position. Rotation of the gear 108 in the opposite direction upon the next actuation of metering unit 140 will move the gear racks through the centered position, releasing the rods to again close the associated valves. Rotation is continued in the opposite direction and the upper gear rack 94 will move to the left and lower gear rack 96 will move to the right so that extensions 98 and 100 engage the extensions 102 on the other rods at opposite corners to move the rods away from the cassette and permit the associated valves 58 and 88 to move to the open position. It will be understood that when gear 108 is not being rotated, the springs 92 urge the gear racks into a centralized position and maintain all the valves in the closed position.

The operation of the metering units 10 and 140 is described hereinafter. The portion of delivery line 20 extending from the fluid container 14 is secured at the entry port 82. The portion of delivery line 20 extending to the patient is secured to the exit port 84. Without pivotal motion of frame 24 or rotation of gear 108, the valves in the cassette 26 are all retained in the closed position, preventing fluid flow from the container to the patient.

If frame 24 is pivoted to angle $\theta_2$ and gear 108 is rotated clockwise as viewed in FIG. 6, the entry valve 86 and exit valve 64 will be open. This will permit fluid to flow from the container at the higher pressure head through the entry port 82 and into the second compartment 80. As the fluid flows into the second compartment 80, it deflects the flexible diaphragm 70 toward the inner surface of the reservoir portion 36 of half 28 until the second compartment has a volume substantially equal to the entire reservoir 76 and the first compartment 78 has substantially zero volume. Were fluid present in the first compartment 78, the fluid would be at a lower pressure head than the fluid in the second compartment 80 with the entry valve 58 in the closed position. The fluid entering the second compartment would urge the fluid in the first compartment through the open exit valve 64 and to the exit port 84 for infusion into the patient.

Upon activation of the metering units by pivoting frame 24 to angle $\theta_1$ or gear wheel 108 in the opposite, counterclockwise direction, the entry valve 58 and exit valve 88 are opened. Simultaneously, the exit valve 64 and entry valve 86 are again moved to the closed position. Fluid from the container 14 then flows through the entry port 82 and into the first chamber 78. The relatively higher pressure head of the fluid entering the first compartment urges the flexible diaphragm 70 toward the inner surface of the reservoir portion of half 30, forcing the fluid in the second compartment past the exit valve 88 and into the exit port 84 for infusion into the patient.

It is clear that alternate opening and closing of the pairs of valves, entry valve 58 and exit valve 88 forming the first pair and exit valve 64 and entry valve 86 forming the second pair, upon each activation of the metering unit permits a predetermined quantity of fluid having a volume substantially equal to the volume of the reservoir 76 to be metered into the exit port 84 for infusion. The channels 38 and 42 are offset to minimize pressure head variation in the channel volume. If the channels were centered, the channels in the two cassettes would be facing each other across the diaphragm. Higher pressure fluid in one channel could deflect the diaphragm into the other channel, increasing the volume of the higher pressure channel and decreasing the volume of the lower pressure channel. This could result in pressure dependent delivery rates.

In the preferred embodiment, the volume of the reservoir 76 is approximately 0.1 cc for adults, and 0.05 cc for pediatric applications. Therefore, upon each activation of the metering units 10 and 140 with a 0.1/cc reservoir, 0.1 cc of fluid is delivered for infusion into the patient. A predetermined rate of fluid may then readily be infused by the metering units 10 and 140 by activating the units at a predetermined frequency. If a steady flow is desired, a small reservoir volume and large cycle rate can be used to reduce the time delay between fluid delivery. The volume of fluid delivered for infusion into the patient may also readily be ascertained by summing the number of activations of the metering units 10 and 140.

The metering units 10 and 140 of the present invention form a significant improvement over the prior art. Neither unit relies upon pinch control to control the flow rate. Therefore, the inaccuracies associated with this technique can be eliminated. No drip chamber need be employed, eliminating the potential inaccuracy caused by the variation in drop volume. The cassette 26 is formed of two equal halves which permits a much simpler construction than found in the prior art. While the halves 28 and 30 are identical in the preferred construction, they may be of any shape suitable to perform their function. The reservoir portion 36 can be of spherical shape, for example. The reservoir portions on each half need not be equally shaped. The only restriction to reservoir shape is the necessity of the diaphragm 70 to be capable of urging a predetermined volume of fluid from each compartment. The delivery of fluid is also relatively independent of pressure head. The pressure head at the entry port need only be sufficient to deflect the diaphragm. In the first embodiment, the cassette itself may be moved to meter fluid therethrough. The prior art devices have not been capable of this type of motion.

The provision of a single entry and exit port simplifies the connection of the metering unit in an additive system. This will prevent manipulation error and reduce the time required to prepare an additive system for operation. The provision of spring loaded rods, or other means permit the valves to be maintained in the closed position when the metering unit is not activated. This prevents infusion of fluid when the metering unit is not activated. If desired, the valves can be opened with free flow of fluid through the cassette controlled by a conventional pinch control or similar device on delivery line 20. The provision of a reservoir having a relatively small fluid volume permits the metering units to achieve a relatively steady flow of fluid for infusion as the delivery of a number of small volumes on a discrete basis permits a relatively steady average flow rate to be established.

The third embodiment of the present invention is formed by metering unit 200 which is illustrated in FIGS. 8–21 and described hereinafter. The metering unit 200 also provides for volumetrically controlled introduction of fluid from a container 14 to the patient 22.

The metering unit 200 includes a control section 202, an actuating frame 204 and a cassette 206. The cassette 206 comprises two halves 208 and 210. In the preferred construction, the halves 208 and 210 are identical to reduce manufacturing cost. The detailed discussion of cassette half 208 hereinafter applies to half 210 as well.

The half 208 includes an inner face 212 forming one side thereof as best seen in FIG. 10. The inner face 212 is formed predominantly in two offset parallel planes 286 and 292. An outer face 214 is formed on the opposite side as best shown in FIGS. 9 and 11. A concave reservoir portion 216 is formed within the inner face 212 as best seen in FIGS. 10 and 11. Dual parallel first channels 218 are also formed in the inner face 212 which extend from a first orifice 220 to the reservoir portion 216. Dual parallel second channels 222 are similarly formed within the inner face 212 which extend from the reservoir portion 216 to a second orifice 224. The first channels 218 and second channels 222 extend into the surface 226 of the reservoir portion 216. The channels 218 and 222 are connected by circular channels 228 and 230 also formed in surface 226.

A cylindrical stem 232 extends from one end of the cassette half 208 which includes a port 234. The cylindrical stem 232 includes lugs 236 to secure a male Luer Lock fitting. In the alternative, a tube can be solvent bonded within stem 232 or slip fit over the exterior of stem 232. In the preferred construction, the cassette halves 208 and 210 are injection molded with a core pin to facilitate the formation of the multi-planar inner surface 212. The end of half 208 opposite stem 232 is formed with a recess 238. The recess 238 is adapted to receive the stem on the half 210 when the halves form the cassette 206.

The outer face 214 of half 208 is formed with two concave seal surfaces 240 and 242 concentric with orifices 220 and 224. A first passage 244 extends through the cassette half 208 opening through seal surface 240 a distance from orifice 220. The passage also opens into the port 234 through stem 232 and through the inner face 212 of the cassette half 208. A similar, second passage 246 opens through the seal surface 242 and through the inner face 212.

Annular notches 248 and 250 are formed in the outer face 214 concentric with the seal surfaces 240 and 242, respectively. Outwardly extending ridges 252 and 254 are provided with annular outwardly facing surfaces 256 and 258.

An entry valve 260 and exit valve 262 are provided with lips 264 for sealing engagement within the annular notches 248 and 250, respectively, as best seen in FIG. 9. Each valve 260 and 262 includes a convex sealing face 266. Face 266 of valve 260 is movable into sealing engagement with the seal surface 240 to prevent flow between the first passage 244 and first orifice 220. Face 266 of valve 262 is movable into sealing engagement with seal surface 242 to prevent flow from second passage 246 to second orifice 224.

The valves 260 and 262 include lips 268 on their opposite side. Caps 270 are provided with annular notches 272 for receiving the lips 268 as seen in FIG. 9. Each cap 270 is provided with a circular ridge 274 for ultrasonic welding between the cap and cassette half which are formed of a plastic. The caps are placed on the cassette half with the valves secured therebetween as shown in FIG. 9. The pieces are then subjected to vibration at a high frequency, approximately 20 kilohertz. The mechanical energy of vibration is directed between the cap and cassette half through the ridge 274. The adjacent areas become liquid from the frictional heat generation. The cap and cassette half are clamped together until the pieces cool, resulting in a secure and fluid tight weld between the cap and cassette half. The caps therefore retain the valves 260 and 262 in close proximity to the cassette half and the valves may be actuated by mechanical action through the aperture 276 in each cap.

The cassette half 208 is formed with alignment pins 278 extending from the inner face 212 on opposite sides of the face. Two alignment holes 280, sized to receive the pins 278, are formed in the inner face on opposite sides of the cassette half.

As noted, the inner face 212 is generally formed in two parallel planes 286 and 292. Curvilinear ridges 282 with planar surfaces 284 extend from plane 292 to plane 286. The surface 288 through which the orifices, passages, channels and reservoir portion are formed lies in plane 286. Surface 290 on either side of surfaces 288 and within the ridges 282 is formed in plane 292. The pins 278 extend from and holes 280 are formed in the surface 290. Curvilinear energy directors 294 extend outwardly from the planar surfaces 284 and the plane 286 on the curvilinear ridges 282.

The inner faces of the two halves 208 and 210 are designed to be secured in a facing relation and separated by a flexible diaphragm 296. The diaphragm 296 is best illustrated in FIG. 14. The diaphragm has a generally curvilinear shape with holes 298 for passage of the alignment pins 278. Two holes 300 permit free communication between the passages 244 and 246 of the two cassette halves. Port 234 and passage 244 of half 208 and passage 246 of half 210 are each sections of an entry port for inflow of fluid. Port 234 and passage 244 of half 210 and passage 246 of half 208 are each sections of an exit port for outflow of fluid. The halves are then ultrasonically welded between the surfaces 284 through energy directors 294.

The cassette halves can also be formed of material other than plastics. The cassette halves can also be secured together by any common means, such as glue, threaded screws, rivets, bolts, or even injection molded together, etc. as best suited for the material used.

When the cassette halves 208 and 210 are in the facing relation with the diaphragm 296 therebetween, the cassette 206 is formed as best seen in FIG. 9. The concave reservoir portions 216 combine to form a concave reservoir 302. The reservoir 302 is separated into a first compartment 304 and a second compartment 306 by diaphragm 296. With the cassette halves secured together, the diaphragm 296 forms an effective seal between the passages, orifices, channels, reservoir portions and remainder of the cassette halves on the surface 288.

When the entry valve 260 and exit valve 262 on half 208 and entry valve 308 and exit valve 310 on half 210 are in the open position, as shown in FIG. 9, fluid flow is permitted through the cassette from one port 234 to the other. The valves illustrated are designed to be open in the absence of an external influence. However, the valves can as readily be closed if desired in the absence of an external influence. When the valves are deflected inward toward the inner face of the half cassette to which they are secured, the valve will close and prevent fluid flow between the associated passage and orifice.

The cassette halves 208 and 210 are preferably constructed with integral finger grip extensions 312 to ease handling of the cassette.

The operation of the cassette 206 is substantially identical to the operation of cassettes 10 and 140 described hereinabove. The use of dual parallel channels 218 and 222 reduces the variance of fluid delivery with head pressure of the fluid within the cassette. If a single channel is employed, and particularly if the channels in the cassette halves are on directly opposite sides of the diaphragm, the pressure in the fluid within the cassette tends to deflect the diaphragm into the channel having the lower pressure fluid. This can result in an increase in the fluid delivered above the quantity determined by the reservoir, with the increase being dependent upon the head pressure of the fluid delivered. The use of multiple passages 244 and 246 minimizes this problem by reducing the unsupported surface area of the diaphragm 296.

The extension of the channels 218, 222 and circular channels 228 and 230 in surface 226 reduces the potential for entrapment of fluid against the surfaces 226 as the diaphragm deflects sufficiently to approach the surfaces 226. Without these channels, ripples can develop in the diaphragm which may retain quantities of fluid within the reservoir portions and result in a delivery of less fluid than desired.

The cassette 206 can be mounted in and actuated by the actuating assembly 204 best illustrated in FIGS. 15–20. The actuating assembly 204 includes a frame 314 firmly secured to the metering unit 200. Spring loaded clamshell clamps 316 are pivoted at one of their ends by pins 318 to one end of frame 314. The front of the clamps 316 include hook portions 320 which spread apart when the cassette 206 is inserted between the bars and snap together to retain the cassette within the frame as shown in FIGS. 15–19. The bars are urged together to retain the cassette within the frame by clamshell clamp retention springs 322 passing through apertures 323 in the frame 314.

Four actuating arms 324, two on each of the clamps 316, are pivoted at their center to pins 319. The forward end of each arm is adapted for contacting one of the four valves employed in cassette 206. A button closure pad 321 is threadedly received in each arm 324 for actual contact with the valves. The pads 321 can be screwed in and out of the arms to provide adjustments. The pivoting of the forward end of an arm inward closes the associated valve when the cassette 206 is clamped by clamps 316. Arm tension springs 325 are positioned through apertures 327 in the frame 314. The springs 325 act on the arms between their pivot axis and valve contacting end to urge the arms away from the valves of the cassette 206. The end of each arm opposite the valve contacting end has a cam follower 329 mounted thereon.

A motor 326 is mounted on the frame 314 for rotating a drive shaft 328 centrally located within the frame 314 at one end. The drive shaft 328 mounts cams 330 and 332 and a position disk 334. An optical interrupter assembly 336 is mounted to sense the passage of portions of the position disk to sense the rotational position of the drive shaft 328. The cams 330 and 332 are designed to pivot the actuating arms 324 to alternately open and close each valve on the sides of the cassette. The cams 330 and 332 are designed so that only one of the two valves controlled by a given cam can be in the open position at a given time. This can be accomplished by having a single raised camming surface on each of the cams 330 and 332 which can allow only one of the arms controlled by each of the cams to be moved into engagement with the valve which it controls.

In the preferred construction, the cams 330 and 332 are designed to operate the valves in a three stage sequence. In the first stage, the cams 330 and 332 will initially be positioned to cause a first pair of valves to be open and a second pair to be closed. The cams will then close all the valves in the second stage. Finally, the cam will open the second pair of valves and close the first pair of valves in the third stage. This sequence has several critical advantages. First, the sequence permits great accuracy in fluid delivery through the cassette. That is, upon each movement of the cams to open a pair of valves, a volume limited to the volume of the fluid chamber in the cassette will be delivered to the patient. Secondly, should any component in the metering unit fail with a stoppage of the drive shaft 328 in a given position, the maximum volume of fluid which could be delivered to the patient after the malfunction is again the volume of the chamber in the cassette.

Figure 21:
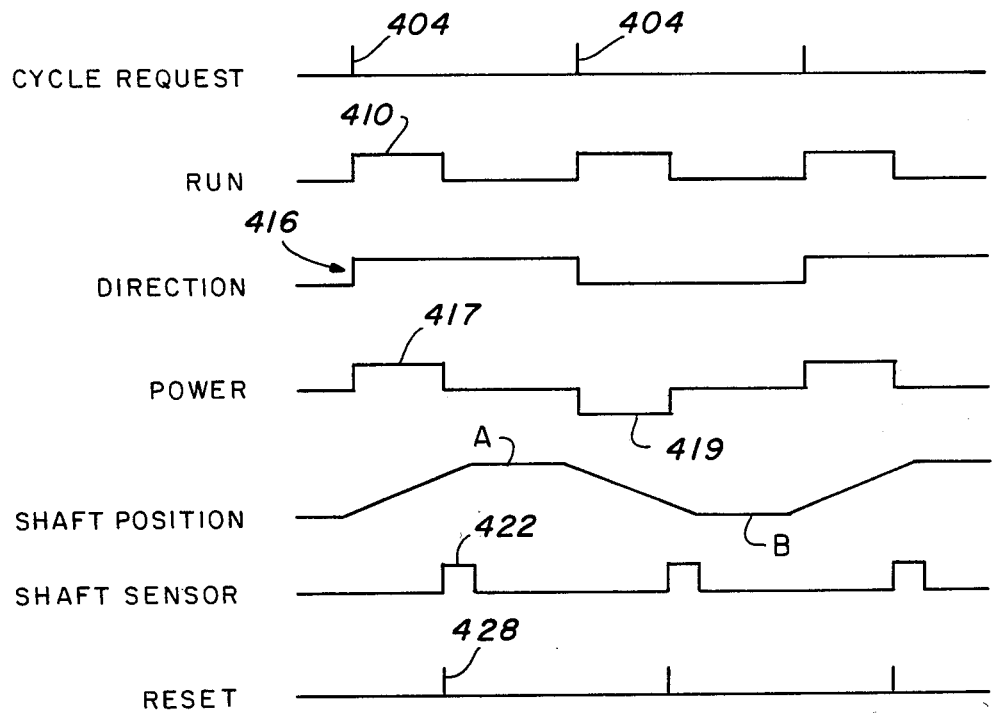
FIG. 21 illustrates the relative time relationships of signals within the electronic control circuit.

A control system 400 is secured on the motor 326 to control the operation of the actuating assembly 204. This control system is best described with reference to FIGS. 20 and 21. FIG. 20 illustrates a block diagram of the control system. FIG. 21 illustrates the time relationships of activity in the control system.

An electronic clock circuit 402 generates a clock pulse or cycle requests 404 at uniform time intervals. The frequency of the cycle requests is determined by the desired fluid delivery rate. A cycle request 404 is generated when it is desired to deliver a volume of fluid to the patient equivalent to the volume of the delivery chamber in the cassette.

The cycle request 404 is transferred to a set/reset bistable circuit 406 over line 408. The cycle request enters the circuit 406 at the S terminal, thereby setting the circuit and causing the circuit 406 to generate a run signal 410 over line 412.

A motor driver circuit 414 receives the run signal 410 and applies power to the motor 326 to rotate the shaft 328 and cams 330 and 332. The circuit 414 can cause rotation of shaft 328 in both directions. The power to rotate the shaft 328 in a first direction is represented by a position signal 417. The rotation in the opposite direction is represented by negative signal 419. The direction of rotation of motor 326 is determined by the value of a direction signal 416 delivered over line 418 to the motor driver circuit 414 from a trigger bistable circuit 420. The motor 326 moves the shaft between first position A and second position B. In first position A, one set of valves is open and one closed. In second position B, the other set of valves is open and the first set closed.

Motor 326 continues to run until the optical interrupter assembly 336 senses motion of the position disk 334 sufficient for the shaft 328 to move between positions A and B to alter the positions of all four valves in the cassette. The interrupter assembly 336 then delivers a completion of motion signal 422 over line 424 to a pulse bistable circuit 426. The pulse bistable circuit 426 then generates a reset signal 428 which travels over line 430 to the set/reset bistable circuit 406 to reset the circuit 406. When the circuit 406 is reset, the run signal 410 is deactivated and the motor driver circuit 414 therefore prevents further motion in the drive motor 326.

The trigger bistable circuit 420 alternates between on and off values each time the set/reset bistable circuit 406 receives a cycle request 404. This causes the motor driver circuit 414 to alternately apply opposite polarity to the motor, causing the rotation of the motor, and hence the drive shaft 328 and cams 330 and 332 to be in opposite directions each time a cycle request 404 is generated. The shaft therefore alternates between position A and position B.

The cassette 206 can be removed from the actuating assembly 204 by rotating the spreader lever 432. The spreader lever 432 rotates the spreader shaft 434. This, in turn, rotates spreader cams 436 and 438 on the shaft 434. The cams urge the clamshell clamps 316 apart to permit removal of the cassette 206. A clamshell locking cam 440 can be secured on the shaft 434 to lock the cassette 206 within the actuating assembly 204 by preventing motion of the clamshell clamps 316. A clamshell locking shaft and clevis assembly 442 can be used to remotely lock the cassette within the actuating assembly.

In the operation of unit 200, the delivery line 20 extending from the fluid container is secured, for example, at the port 234 of the cassette half 208. The delivery line 20 extends from the exit port 234 in the second cassette half 210 for delivery to the patient. However, it would be equally satisfactory to reverse the position of the ports since the entire cassette is symmetrical.

The motor 326 can be activated to move cams 330 and 332 to position A so that the entry valve 260 and exit valve 310 are opened. The exit valve 262 and entry valve 308 are closed in position A. This will permit fluid to flow from the container at a higher pressure head through the port 234, first passage 244, first orifice 220 and into the channels 218 of half 208 for entry into the first compartment 304. As the fluid flows into the first compartment, the diaphragm 296 deflects into the second compartment 306, driving any fluid within the second compartment through the first channels 218, through the first passage 244 and out the port 234 of the cassette half 210 for delivery to the patient.

The motor 326 is then activated to move cams 330 and 332 to close all the valves intermediate positions A and B. As the motor 326 continues to move to position B, cams 330 and 332 close entry valve 260 and exit valve 310 and open exit valve 262 and entry valve 308. This permits fluid to flow from the port 234 and first passage 244 of cassette half 208 into the second passage 246 of the cassette halve 210 through a hole 300. The flow continues through the second channels 222 of cassette half 210. The fluid then flows into the second compartment 306, deflecting the diaphragm 296 in the opposite direction to fill the volume of the reservoir 302. The fluid in the first compartment 304 is driven from the reservoir 302 through the second channels 222 in cassette half 208 through the second orifice 224 in cassette half 208, through the passages 246 and 244 in the cassette halves 208 and 210, respectively, to the port 234 in the second cassette half 210 for delivery to the patient.

It is clear that the alternate opening and closing of the pairs of valves upon each actuation of the cassette by the actuating assembly 204 permits a predetermined quantity of fluid having a volume substantially equal to the volume of the reservoir 302 to be metered to the patient.

In the preferred construction, the limits of motion of shaft 328 are 180° apart. The surface of cams 330 and 332 are designed so that each set of valves is open for about 80° of travel from one limit with the 20° in midmotion with all valves closed. Thus, each time the valve positions are changed, there is a guaranteed period when all valves are closed. The device prevents all valves from being open simultaneously, even in the event of a failure of the electronic circuits.

The cassette 206 with actuating assembly 204 can be operated in a manner identical to metering units 10 and 140 to achieve similar advantages. The valves described can be substituted for by any functional equivalent, for example rotary valves. If desired, the valves of metering units 10, 140 and 200 can be provided with magnetic material for actuation by a magnetic source, such as an electromagnet. Pneumatic operation of the valves is also possible to effect opening and closing of the valves. The preferred material of construction of the diaphragms and valves employed in the metering units described hereinabove is silicon. This material provides a good shelf life, relative insensitivity to temperature and good mechanical flexibility. However, latex rubber, urethane or a Krayton material or other suitable material can be used.

The control system 400 of metering unit 200 is employed to operate the metering unit to deliver a desired flow rate entered into the delivery controls 370 by the operator. The control system 400 can also provide alarms to alert the operator to any condition desired. A display 372 can be incorporated to represent the delivery system, in particular a representation of a system employing a primary and secondary fluid. With a primary and secondary fluid the display can illustrate the particular source delivering fluid at a given moment. The display can also provide an instantaneous read out of the volume of fluid infused to the patient and the remaining volume to be infused.

Although three embodiments of the present invention have been illustrated in the accompanying Drawings and described in the foregoing Detailed Description, it will be understood that the invention is not limited to the embodiments disclosed, but is capable of numerous rearrangements, modifications and substitutions of parts and elements without departing from the scope and spirit of the invention.

We claim:

1. A cassette for metering a fluid therethrough, comprising:

first and second integrally molded halves secured in facing relation, each of said halves being constructed to form: a reservoir portion; at least one inlet channel and at least one outlet channel each extending from the reservoir portion; and inlet and outlet port sections; the inlet channel and inlet port section of each being interconnected by an inlet orifice and the outlet channel and the outlet port section of each being interconnected by an outlet orifice, the reservoir portions of each half forming a reservoir and said port sections of each half forming a single entry port and a single exit port;

a flexible diaphragm means positioned between said first and second halves for dividing the reservoir into first and second compartments;

first entry valve means and first exit valve means associated with said first half, said first entry and exit valve means being movable between an open position permitting fluid flow through the inlet and outlet orifices of said first half, respectively, and a closed position to prevent flow through the inlet and outlet orifices, respectively;

second entry valve means and second exit valve means associated with said second half, said second entry and exit valve means being movable between an open position permitting fluid flow through the inlet and outlet orifices of said second half, respectively, and a closed position to prevent fluid flow through the inlet and outlet orifices, respectively;

fluid entering said entry port flowing through the inlet orifice and inlet channel of said first half into the first compartment when said first entry valve means and said second exit valve means are open and said first exit valve means and second entry valve means are closed, to move said diaphragm means to force the fluid in the second compartment through the outlet channel and outlet orifice of said second half to the exit port; and fluid entering said entry port flowing through the inlet orifice and inlet channel of said second half into the second compartment when said second entry valve means and said first exit valve means are open and said first entry valve means and second exit valve means are closed, to move said diaphragm means to force the fluid in the first compartment through the outlet channel and outlet orifice of said first half to the exit port, the fluid displaced from each of the first and second compartments having a predetermined volume.

2. The apparatus of cliam 1 wherein said first and second halves are identical.

3. The apparatus of claim 1 further including activating means for opening and closing each of said valve means.

4. The apparatus of claim 3 wherein said activating means prevents any two valve means associated with the same compartment from being in the open position simultaneously to prevent uncontrolled flow through the apparatus.

5. The apparatus of claim 3 wherein said activating means includes:
a plurality of rod means positioned adjacent the valve means, one rod means for contacting each of said valve means, and means for movement of the rods to open said first entry valve means and said second exit valve means, and means for movement of the rods to open said second entry valve means and said first exit valve means.

6. The apparatus of claim 6 wherein said activating means permits all of the valve means to be in the closed position simultaneously to prevent fluid flow through the apparatus.

7. The apparatus of claim 3 wherein said activating means includes:
frame means for being secured in a fixed relation to said cassette;
clamp means for securing said first and second halves in a fixed relation to said frame means;
a plurality of bar means supported for motion relative to said frame means, each of said bar means contacting one of said valve means to operate the valve means between the closed and opened positions; and
drive means to move said bar means to move said first entry valve means and said second exit valve means to the open position and said second entry valve means and said first exit valve means to the closed position, said drive means subsequently moving said rod means to move said second entry valve means and said first exit valve means to the open position and said first entry valve means and said second exit valve means to the closed position.

8. The apparatus of claim 8 wherein said drive means includes at least one camming surface operating the bar means to open and close the valve means so that simultaneous positioning of all valve means in the open position is prevented.

9. The apparatus of claim 9 wherein said first and second halves are identical.

10. The apparatus of claim 1 wherein each inlet and outlet channel is divided into a plurality of adjacent sub-channels to reduce variation of the channel cross section at different fluid pressure by varying deflection of the diaphragm means into the channels.

11. The apparatus of claim 1 wherein said reservoir portions include grooves formed within the surfaces thereof to prevent trappage of fluid by the diaphragm means, and said grooves surround a central area which is not traversed by grooves or channels.

12. A cassette for metering a fluid therethrough comprising:
first and second integrally molded halves having confronting surfaces secured in facing relation, each of said first and second halves being constructed to form a reservoir portion, at least one inlet and at least one outlet channel extending along the confronting surface from said reservoir portion and inlet and outlet port sections, the inlet channels and inlet port section being interconnected by an inlet orifice, and the outlet channels and outlet port section being interconnected by an outlet orifice, each of said first and second halves forming a seal surface about each of the orifices, the reservoir portions of said first and second halves forming a reservoir and the inlet port section of each half and the outlet port section of each half combining to form entry and exit ports, respectively;
a flexible diaphragm positioned between said first and second halves so that the reservoir is divided into first and second compartments;
first entry and exit valves mounted on said first half adjacent the entry and exit orifices, said first entry and exit valves having convex resilient sealing surfaces and being movable from an open position permitting fluid flow through said inlet and outlet orifices, respectively, to a closed position in sealing contact with the seal surfaces about the orifices to prevent flow therethrough;
second entry and exit valves mounted on said second half adjacent the entry and exit orifices, said second entry and exit valves having convex resilient sealing surfaces and being movable from an open position permitting fluid flow through said inlet and outlet orifices, respectively, to a closed position in sealing contact with the seal surfaces about the orifices to prevent flow therethrough;
fluid entering said entry port flowing through the inlet orifice and inlet channel of said first half into the first compartment when said first entry valve and second exit valve are open, to move said flexible diaphragm to force fluid in the second compartment through the outlet channel and outlet orifice of said second half to the exit port; and
fluid entering said entry port flowing through the inlet orifice and inlet channel of said second half to the second compartment when said second entry valve and first exit valve are open, to move said flexible diaphragm to force fluid in the first compartment through the outlet channel and outlet orifice of said first half to the exit port, the fluid displaced from each of the first and second compartments having a predetermined volume.

13. The apparatus of claim 13 further comprising:
activating means for alternately opening and closing each of said valves, said first entry valve and said second exit valve being in the same position simultaneously and said second entry valve and said first exit valve being in the opposite position simultaneously, said activating means preventing all said valves from being open simultaneously.

14. The apparatus of claim 14 wherein said activating means includes:

a frame mounted for pivotal motion relative to said first and second halves when secured in facing relation;

a plurality of rods slidably supported in said frame, one of said rods being positioned adjacent each of said valves;

spring means associated with each of said rods for urging each of said rods into contact with the adjacent valve; and pivotal motion of said frame in a first direction relative to said first and second halves inducing motion in said rods to open said first entry valve and said second exit valve with said second entry valve and said first exit valve in the closed position, pivotal motion of said frame relative to said first and second halves in the opposite direction inducing motion in said rods to open said second entry valve and said first exit valve with said first entry valve and said second exit valve in the closed position.

15. The apparatus of claim 15 wherein said spring means urges said frame and said plurality of rods into a position wherein all of said valves are in the closed position to prevent fluid flow therethrough.

16. The apparatus of claim 14 wherein said activating means includes:

a frame secured in a fixed relation to said first and second halves when secured in facing relation;

a plurality of rods slidably mounted on said frame, one of said rods being movable into contact with each of said valves;

spring means associated with each of said rods for urging said rods into contact with each of said valves;

a gear mounted for rotation about an axis fixed relative to said frame;

gear rack means mounted for slidable motion relative to said frame and having teeth for engaging the teeth on said gear, said gear rack means having extension means thereon for contacting each of said rods; and rotation of said gear in a first direction moving said gear rack means and selected ones of said rods to permit said first entry valve and said second exit valve to be in the open position and said second entry valve and said first exit valve to be in the closed position, rotation of said gear in the opposite direction moving said gear rack means and selected ones of said rods to move said second entry valve and said first exit valve to the open position and said first entry valve and said second exit valve into the closed position.

17. The apparatus of claim 17 wherein said spring means center said gear and said gear rack means so that each of said valves is maintained in the closed position until application of a force to rotate said gear.

18. The apparatus of claim 14 wherein said activating means includes:

a frame;

at least one clamp pivoted to said frame;

spring means for urging said clamp to clamp the cassette in a fixed relation to said frame and clamp;

a plurality of arms mounted for motion relative to said frame, each arm for activating one of said valves; and drive means for operating said arms to alternately open and close said valves, said drive means defining at least one camming surface for contacting selected ones of said arms, the camming surface preventing all valves from being in the open position simultaneously.

19. The apparatus of claim 13 wherein each of said first and second halves include a plurality of inlet and outlet channels extending into the half for preventing cross-sectional variation in the channels by diaphragm deflection.

20. The apparatus of claim 13 further having grooves formed within the surface of the reservoir portions on each half to prevent trappage of fluid by the diaphragm, and having an ungrooved central surface area.

21. An apparatus for metering a fluid therethrough, comprising:

a cassette formed from substantially identical first and second integrally-molded halves having inner sides in facing relation and having a flexible diaphragm therebetween, each of said first and second halves being constructed to form a reservoir portion in the inner side thereof, at least two parallel entry channels and at least two parallel exit channels extending from said reservoir portion and entry and exit port sections, said entry channels and entry port section being interconnected through an entry orifice, said exit channels and exit port being interconnected through an exit orifice, the outer side of said first and second halves forming seal surfaces about each of said orifices, the reservoir portion of each of said first and second halves combining to form a reservoir divided into first and second compartments by said flexible diaphragm, each of said entry and exit port sections combining to form entry and exit ports, respectively;

grooves formed in each of said reservoir portion surfaces to prevent trapping of fluid in the reservoir, surrounding a central area of ungrooved reservoir wall;

flexible first entry and exit valves operatively associated with the outer side of said first half, each of said first entry and exit valves having a seal face thereon for sealing engagement with the seal surface about said entry and exit orifices of said first half, respectively, each of said first entry and exit valves being positionable in the open position to permit fluid flow through said entry and exit orifices, respectively, and in the closed position, preventing flow of fluid through said entry orifices, respectively;

flexible second entry and exit valves operatively associated with the outer side of said second half, each of said second entry and exit valves having a seal face thereon for sealing engagement with the seal surface about the entry and exit orifices of said second half, respectively, each of said second entry and exit valves being positionable in the open position permitting fluid flow through the entry and exit orifices of said second half, respectively, and in a closed position, preventing flow of fluid through said entry and exit valves of said second half, respectively; and said first entry valve and said second exit valve forming a first valve pair and said second entry valve and said first exit valve forming a second valve pair, fluid entering said entry port flowing through the entry orifice and entry channels of said first half into the first compartment when said valves of said first valve pair are open and said valves of said second pair are closed, to force fluid in said second compartment through the exit channels and exit orifice of said second half to said exit port; fluid entering said entry port flowing through the entry orifice and entry channels of said second half into the second compartment when said valves of said second valve pair are open and said valves of said first pair are closed, to force the fluid in the first compartment through the exit channels and exit orifice of said first half to the exit port, the fluid displaced from each of the first and second compartments having a predetermined volume.

22. The apparatus of claim 22 further comprising activating means for opening and closing each of said valves, said valves of said first valve pair being in the same position and said valves of said second valve pair being in the same position.

23. The apparatus of claim 23 wherein said activating means includes:
a frame mounted for pivotal motion relative to said cassette;
four rods slidably supported in said frame, one of said rods being positioned adjacent each of said valves;
spring means interposed between said frame and each of said rods to urge each of said rods into contact with the adjacent valve, said spring means urging each of the rods to contact the adjacent valve to maintain the valve in a closed position to prevent fluid flow therethrough; and
pivotal motion of said frame in a first direction releasing selected ones of said rods from the adjacent valves to open said first pair of valves while maintaining said second pair of valves in the closed position, said frame being pivotal in the oppposite direction to release selected ones of said rods to move said second pair of valves to the open position while maintaining said first pair of valves in the closed position.

24. The apparatus of claim 23 wherein said activating means includes:
a frame secured in a fixed relation to said cassette;
four rods slidably mounted to said frame, one of said rods being movable into contact with each of said valves;
spring means associated with each of said rods for urging said rods into contact with each of said valves; and
means for contacting selected ones of said rods to open said first pair of valves while maintaining said second pair closed, and for contacting selected ones of said rods to open said second pair of valves while maintaining said first pair closed.

25. The apparatus of claim 23 wherein said activating means includes:
a frame;
first and second clamps pivotally mounted to said frame and having cassette receiving structure thereon;
spring means for urging said clamps together to clamp the cassette in a fixed relationship to said frame and clamps;
inlet and outlet valve activating arms pivotally mounted on each of said clamps for activating selected ones of said inlet and outlet valves, respectively, said valve activating arms having camming surfaces formed thereon; and
a cam shaft assembly mounted for rotation within said frame and defining at least one camming surface thereon for contacting the camming surfaces of said arms, rotation of said cam shaft assembly alternately opening and closing each of said valves through the valve activating arms and preventing all of said valves from being open simultaneously.

26. A cassette for metering a fluid therethrough comprising:
substantially identical first and second halves secured in facing relation, each of said first and second halves being constructed to form a reservoir portion in the surface facing the other half, inlet and outlet fluid paths, each of said paths having at least two parallel channels formed in the facing surface, said fluid paths extending from opposite sides of the reservoir portion to inlet and outlet orifices formed through the half, inlet and outlet seal surfaces being formed concentrically about the opening of the inlet and outlet orifices, respectively, on the side opposite the facing side, inlet and outlet passages formed through a portion of said inlet and outlet seal surface, respectively, opening on the facing side and a stem having a port formed therein in communication with one of said passages;
the reservoir portions of said first and second halves forming a reservoir and said ports forming entry and exit ports;
a flexible diaphragm for positioning between said first and second halves to divide the reservoir into first and second compartments, said diaphragm further acting as a seal between said first and second halves while permitting fluid communication between the entry port and the inlet passages in said first and second halves and the exit port and said outlet passages in said first and second halves;
first entry and exit valves for operative association with said first half, said first entry valve being movable from an open position permitting fluid flow from said inlet passage through the inlet orifice of the first half, and said first exit valve being movable from an open position permitting fluid flow between said outlet orifice and the outlet passage of the first half, to a closed position in sealing contact with the seal surfaces about the respective orifices to prevent flow therethrough;
second entry and exit valves for operative association with said second half, said second entry valve being movable from an open position permitting fluid flow from said inlet passage through said inlet orifice of said second half of said second exit valve being movable from an open position permitting fluid flow between said outlet orifice and the outlet passage of the second half, to a closed position in sealing contact with the seal surfaces about the respective orifices to prevent flow therethrough;
whereupon opening of the first entry valve and the second exit valve, fluid enters said entry port flowing through the inlet passage, inlet orifice and inlet fluid path of said first half into the first compartment to move said flexible diaphragm to force fluid in the second compartment through the outlet fluid path, outlet orifice and outlet passage of said second half to the exit port and;
whereupon opening of the second entry valve and the first exit valve, fluid enters said entry port flowing through the inlet passage, inlet orifice and inlet fluid path in said second half to the second compartment to move the flexible diaphragm to force fluid in the first compartment through the outlet fluid path, outlet orifice and outlet passage of said first half to the exit port, the fluid displaced from each of the first and second compartments having a predetermined volume.

27. The apparatus of claim 27 further comprising:
activating means for operating said valves in at least three conditions, the first condition being with said first entry valve and said second exit valve open and said second entry valve and first exit valve closed, the second condition being with all valves closed and the third condition with said first entry valve and said second exit valve closed and said second entry valve and first exit valve open.

28. The apparatus of claim 27 wherein the channels in each half extend into the surface of the reservoir portion to prevent trappage of fluid by the diaphragm.

29. The apparatus of claim 27 further having grooves formed within the surface of the reservoir portion on each half to prevent trappage of fluid by the diaphragm, and wherein a central planar area of the reservoir portion surface is not traversed by grooves or channels.

30. The apparatus of claim 27 wherein said cassette halves are secured in facing relationship by ultrasonic bonding, the facing surfaces of said halves having cooperating energy directors and ridges surrounding the valve and reservoir area.

31. The apparatus of claim 27 further having finger grips on said first and second halves.

32. The apparatus of claim 27 further comprising at least one pin extending from the facing surface of one of said halves for insertion within at least one hole in the other of said halves to align the halves in facing relationship.

33. The apparatus of claim 28 wherein said activating means comprises:
a frame;
clamps pivotally mounted on said frame for pivotal motion to insert said cassette betwen said clamps;
spring means for urging said clamps together to retain the cassette between said clamps;
a drive shaft rotatably mounted on said frame;
motor means for rotating said drive shaft;
actuating arms pivotally mounted on said clamps for actuating said valves on said cassette;
a plurality of cams mounted on said drive shaft for pivoting said actuating arms, said cams being positioned so that all valves cannot be open simultaneously to permit a controlled fluid flow through the cassette; and
means for sensing the angular position of said drive shaft.

34. The apparatus of claim 34 further comprising means for separating said clamps to permit removal of said cassette.

35. The apparatus of claim 34 wherein said spring means comprise at least one spring secured between said clamps for urging the clamps together to retain the cassette.

36. An apparatus for activating a cassette, the cassette having a central metering chamber divided into first and second compartments by a flexible diaphragm, inlet and outlet ports and at least four fluid flow paths comprising an inlet flow path from the inlet port to each of the two compartments and an outlet flow path from each of the two compartments to the outlet port, each flow path having valve means activatable between open and closed position for blocking fluid flow along the flow path in the closed position, said apparatus comprising:
a frame;
holdng means for securing the cassette in a fixed relationship to said frame;
inlet and outlet valve activating arms operatively connected to said frame for activating said valves, said valve activating arms having camming surfaces formed thereon; and
a cam shaft assembly mounted for rotation within said frame and defining at least one camming surface thereon for contacting the camming surfaces of said arms, rotation of said shaft assembly opening and closing each of said valves through the valve activating arms in a predetermined sequence and preventing all of said valves from being in the open position simultaneously.

37. An apparatus for activating a cassette, the cassette having a metering chamber divided into a first and second compartment by a flexible diaphragm, inlet and outlet ports and four fluid flow paths comprising an inlet flow path from the inlet port to each of the two compartments and an outlet flow path from each of the two compartments to the outlet port, each flow path having valve means activatable between open and closed positions for blocking fluid flow along the flow path in the closed position, said apparatus comprising:
a frame;
first and second clamps pivotally mounted to said frame and having cassette receiving structure thereon;
spring means for urging said clamps together to clamp the cassette in a fixed relationship to said frame and clamps;
valve activating arms pivotally mounted on each of said clamps for activating said valve means, said valve activating arms having camming surfaces formed thereon;
a cam shaft rotatably mounted in said frame; and
control means for rotating said cam shaft between first and second limits, first and second camming surfaces being defined on said cam shaft, the first camming surface for contacting the camming surfaces of the arms activating said inlet flow path valve means and said second camming surface for contacting the camming surfaces of the arms activating said outlet flow path valve means, alternate oscillation of said cam shaft by said control means between the first and second limits activating the valve means in the cassette in at least three conditions, the first condition being the opening of a first pair of inlet and outlet valves means on opposite sides of the diaphragm and closing of the other pair, the second condition being the closing of all valve means and the third condition being the opening of the other pair of inlet and outlet valve means and the closing of said first pair of inlet and outlet valves to control the fluid flow through the cassette.

38. A method for activating a cassette, the cassette having a central metering chamber divided into first and second compartments by a flexible diaphragm, inlet and outlet ports and four fluid flow paths comprising an inlet flow path from the inlet port to each of the two compartments and an outlet flow path from each of the two compartments to the outlet port, each flow path having valves activatable between open and closed positions for blocking fluid flow along the flow path in the closed position, said method comprising the steps of:
securing the cassette to a frame;

mounting valve activating means on said frame for activating said valves;

selecting a desired fluid flow rate through the cassette; and oscillating a cam shaft between first and second limits, said cam shaft having at least one camming surface thereon for contacting said valve activating means to activate said valves, the inlet valve to the first compartment and outlet valve from the second compartment being open and the inlet valve to the second compartment and outlet valve from the first compartment being closed when said cam shaft is at the first limit to permit a predetermined quantity of fluid to flow from the second compartment and permit fluid to flow into the first compartment; the inlet valve to the second compartment and outlet valve from the first compartment being open and the inlet valve to the first compartment and outlet valve from the second compartment being closed when said cam shaft is at the second limit to permit a predetermined quantity of fluid to flow from the first compartment and permit fluid to flow into the second compartment, said cam shaft operating said inlet and outlet valve activating means to close all of said valves between the first and second limits, the oscillating of said cam shaft permitting the desired fluid flow rate to pass through the cassette.

* * * * *